US011231369B2

United States Patent
Hayat et al.

(10) Patent No.: US 11,231,369 B2
(45) Date of Patent: Jan. 25, 2022

(54) PORTABLE SINGLE UNIT DEVICE FOR OCHRATOXIN A (OTA) TOXICITY ANALYSIS FOR RICE QUALITY MONITORING

(71) Applicant: COMSATS UNIVERSITY ISLAMABAD, Islamabad (PK)

(72) Inventors: Akhtar Hayat, Lahore (PK); Muhammad Yaqoob Javed, Lahore (PK); Muhammad Umair Safder, Lahore (PK)

(73) Assignee: COMSATS UNIVERSITY ISLAMABAD, Islamabad (PK)

( * ) Notice: Subject to any disclaimer, the term of this patent is extended or adjusted under 35 U.S.C. 154(b) by 0 days.

(21) Appl. No.: 17/005,451

(22) Filed: Aug. 28, 2020

(65) Prior Publication Data

US 2021/0063311 A1 Mar. 4, 2021

(30) Foreign Application Priority Data

Aug. 28, 2019 (PK) ..................... 584/2019

(51) Int. Cl.
*G01N 21/64* (2006.01)
*G01N 33/02* (2006.01)
(Continued)

(52) U.S. Cl.
CPC ......... *G01N 21/6456* (2013.01); *G01N 21/33* (2013.01); *G01N 33/02* (2013.01);
(Continued)

(58) Field of Classification Search
CPC ............... G01N 21/6456; G01N 33/02; G01N 33/56911; G01N 21/33; G01N 2021/1765;
(Continued)

(56) References Cited

U.S. PATENT DOCUMENTS

| 5,178,832 A | * | 1/1993 | Phillips | B01J 20/08 |
| | | | | 422/401 |
| 10,338,631 B1 | * | 7/2019 | Jorden | G01N 21/01 |
| 2007/0117219 A1 | * | 5/2007 | Zabe | B01J 20/3289 |
| | | | | 436/514 |

OTHER PUBLICATIONS

Bueno et al., Portable and low costfluorescence set-up for in-situ screening of Ochratoxin A, Jun. 23, 2016, Taianta 159 (2016) pp. 395-400 (Year: 2016).*

* cited by examiner

*Primary Examiner* — David P Porta
*Assistant Examiner* — Gisselle M Gutierrez
(74) *Attorney, Agent, or Firm* — Oliff PLC

(57) ABSTRACT

A single unit, handheld field portable apparatus and method for analyzing Ochratoxin A (OTA) in rice quality monitoring, based on fluorescence signal output. Aliquots may be analyzed by adding at least one or more reagents to the sample aliquot that reacts selectively with an analyte contained therein. The reaction product, which is selective for the analyte of interest and proportional to its concentration, is measured with an appropriate detector. This enables simple and accurate testing of samples using time honored wet-chemical analysis method in microliter volume regimes while producing remarkably small volumes of waste. The device includes a multipurpose controller board for processing and analysis purpose, a camera which is integrated with the controller, a resistive touch liquid crystal display to view the results, a light emitting diode to emit the UV light, and a power bank. The device may operate using a touch display.

13 Claims, 8 Drawing Sheets

(51) Int. Cl.
  *G01N 33/569*          (2006.01)
  *G01N 21/33*            (2006.01)
  *G01N 21/17*            (2006.01)
  *H04N 5/232*           (2006.01)

(52) U.S. Cl.
  CPC ............... *G01N 33/56911* (2013.01); *G01N 2021/1765* (2013.01); *H04N 5/232933* (2018.08)

(58) Field of Classification Search
  CPC ....... G01N 2201/0221; G01N 21/6486; G01N 33/587; G01N 2333/38; G01N 33/56961; H04N 5/232933; H04N 5/232
  USPC ...................................................... 250/461.1
  See application file for complete search history.

PORTABLE SINGLE UNIT DEVICE FOR OCHRATOXIN A (OTA) TOXICITY ANALYSIS FOR RICE QUALITY MONITORING

FIELD OF THE INVENTION

The present invention relates to defining the levels of OTA in rice quality monitoring and more particularly to a new, inexpensive, portable, hand held means for testing in a field environment for the presence of OTA, using fluorescence output signal.

DISCUSSION ON THE BACKGROUND

The presence of unsafe levels of chemical compounds, toxins and pathogens in food represents a serious threat to the safety of food supply and public health, especially in countries with a poor economy. Among chemical hazards causing foodborne dysfunctions, mycotoxins particularly OTA, pose particular challenges due to their extremely high toxicity at low exposure levels. In spite of significant progress, available methods are expensive; require sample collection and transport at a centralized lab, skilled personnel and specialized equipment for analysis.

Optical spectroscopy finds potential applications in diagnostics, pharmacological testing, food quality assessment, and environmental sensing among numerous other applications. It is convenient for qualitative and quantitative analysis due to its qualities of being easy to use and non-destructive. Spectrometers commonly used in laboratory or industry for sample testing are expensive, large size and require computer setup detector to analyze the information received, consequently spectroscopic testing is restricted to controlled environment laboratory. Recently, a lot of work has been done to generate portable spectrometers, though they also require external computing system for collection and analysis of data. These qualities remarkably raise the price of the system and restrict the system's range. These restrictions lead to approach readily accessible interfacing devices with spectrometer. Mini quantum dot and mobile phone based spectrometers have been reported, however no single hand-held portable device has been reported.

SUMMARY

Machine vision is an automated process that integrates many processes for visual perception, such as image acquisition, image processing, classification, recognition, and decision. Machine vision includes techniques to estimate the characteristics of objects in the image, to measure object geometry, and to interpret information geometry. Machine vision process comprises three main activities such as image capturing, image processing, and image analyzing. In this research, the machine vision system is embedded in a single hand-held portable device. We exhibit first of its type standalone, economical, compactly designed, accurate and unique handheld portable device based on fluorescence signal. The device does not require any desktop computers or laptops with heavy software installation neither Wi-Fi nor internet to work. It is self-assembled minicomputer with multipurpose controller board, a camera which is integrated with controller, a resistive touch crystal display for monitoring results analysis, a light emitting diode to emit the UV light, and a power bank such as a portable power bank. Analysis is performed within a few seconds and we can get the result on the display in term of numbers and percentages. It does not require data interpretation or an expert to operate it. We present a field portable device which is easy to operate and suitable for decentralized and on site testing. We have utilized the device to monitor OTA as a type of mycotoxins for rice quality monitoring.

A single unit, handheld field portable apparatus (1.8) and method for on-site analysis of OTA in rice quality control, using fluorescence output signal (008) is reported. The invention enables simple and accurate testing of samples using time honored wet-chemical analysis methods in microliter volume regimes while producing remarkably small volumes of waste. Two types of nanoprobes including nanoceria (cerium oxide nanoparticles) and nitrogen doped titania (N-doped titanium oxide nanoparticles) are reported to amplify the output generated signal (008). The device includes a multipurpose controller board (1.1) for processing and analysis purpose, a camera (1.3) which is integrated with the controller (1.1), a resistive touch liquid crystal display (1.7) to view the results (008), a light emitting diode to emit (1.5) the UV light (003), and a power bank (1.2) such as a portable power bank. The device may operate with a single click using touch display.

Only a limited number of samples can be tested and predictive or early warning information is missing. This is a significant impediment to provide timely counter-measures, especially in remote locations and in countries with limited resources. The present invention may address this need by providing an apparatus and method suitable for on-site analysis.

BRIEF DESCRIPTION OF THE FIGURES

Other features and advantages of the invention will become apparent from the following description of some forms of embodiment of the invention, given as a nonlimiting example, with the help of the appended diagrams illustrated in the attached drawings, in which.

DETAILED DESCRIPTION OF THE ILLUSTRATED EMBODIMENTS

Figure 1:
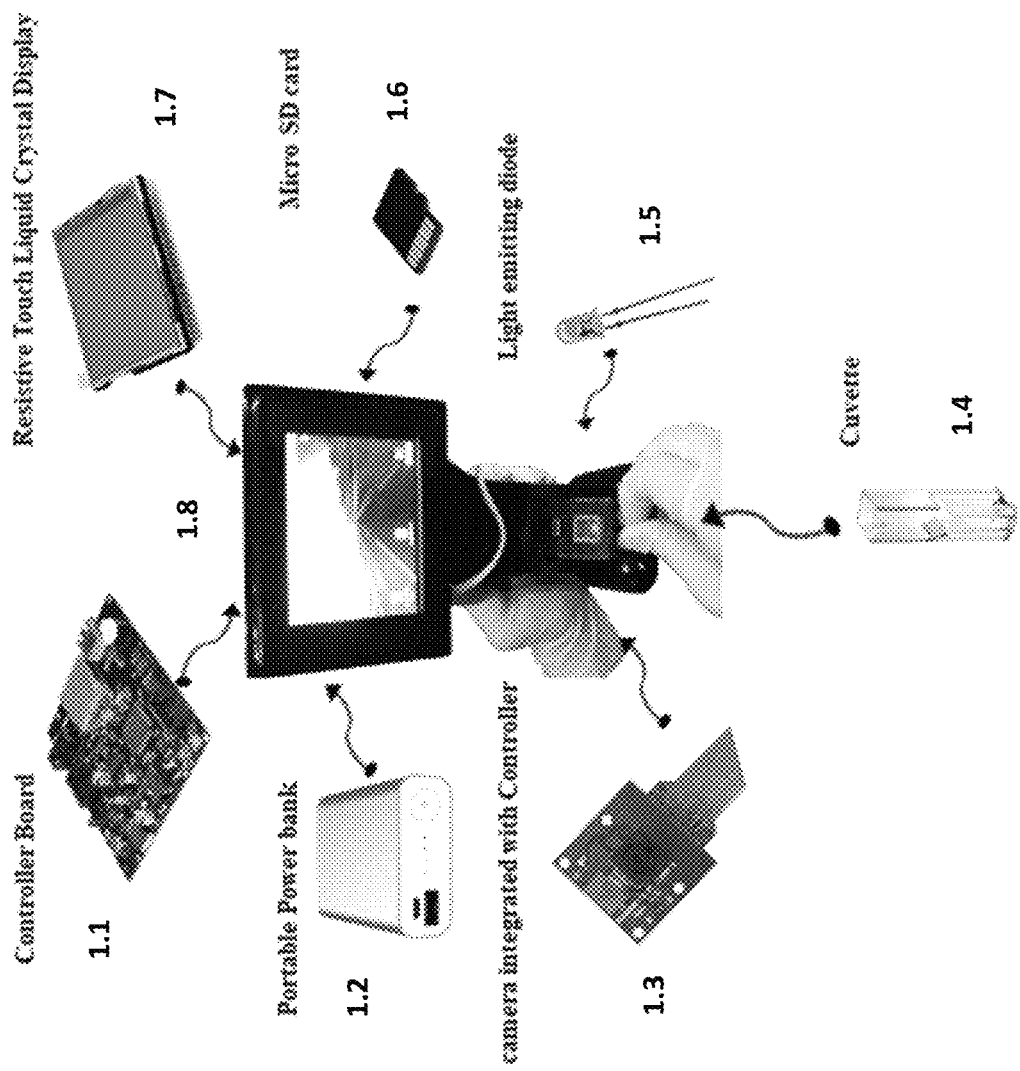
FIG. 1 represents the actual design of prototype and schematic presentation of the hardware components used in the fabrication of the prototype.
Figure 2:
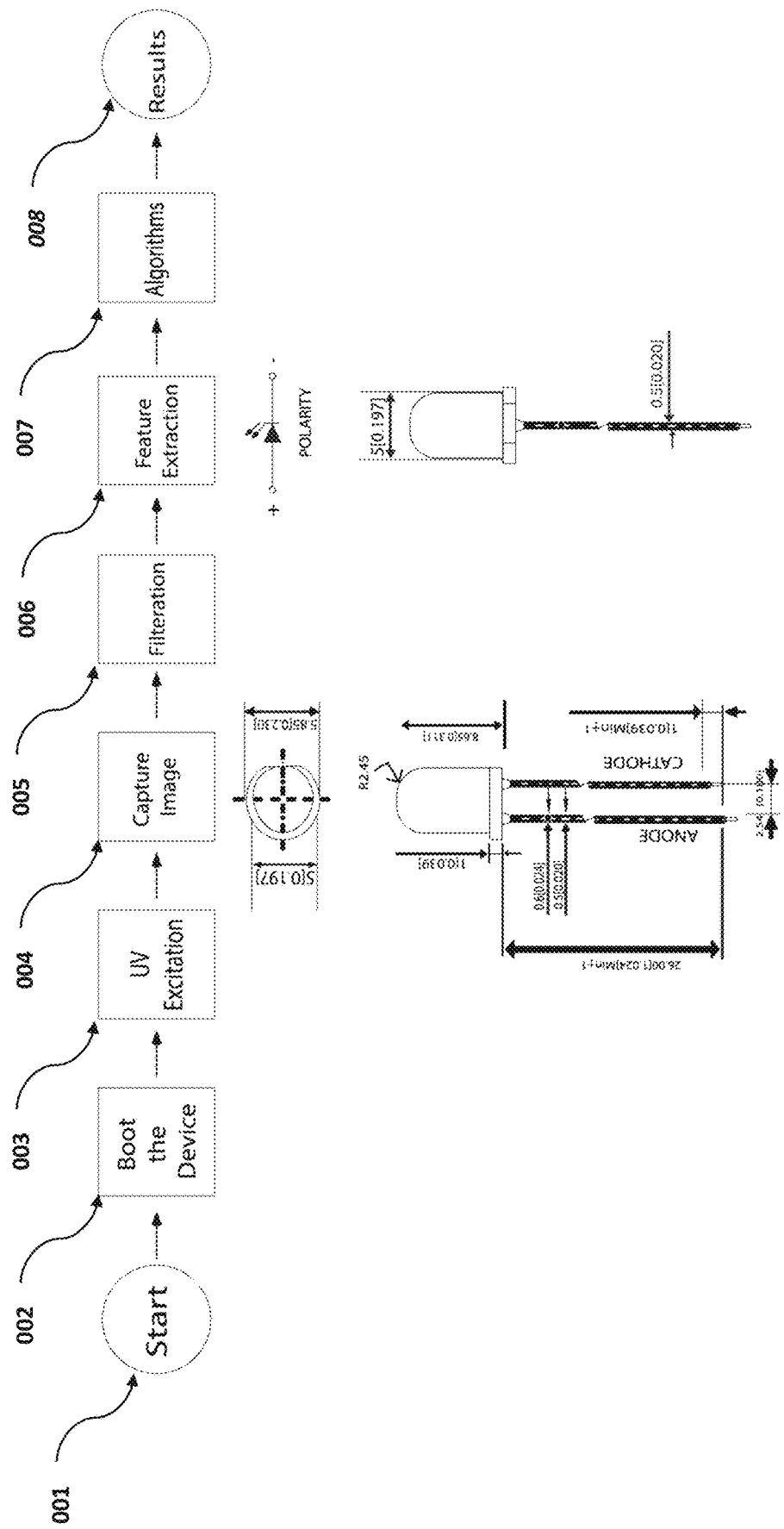
FIG. 2 is a flow chart illustrating the programming and functions to generate output signal and subsequently the display for users.
Figure 3:
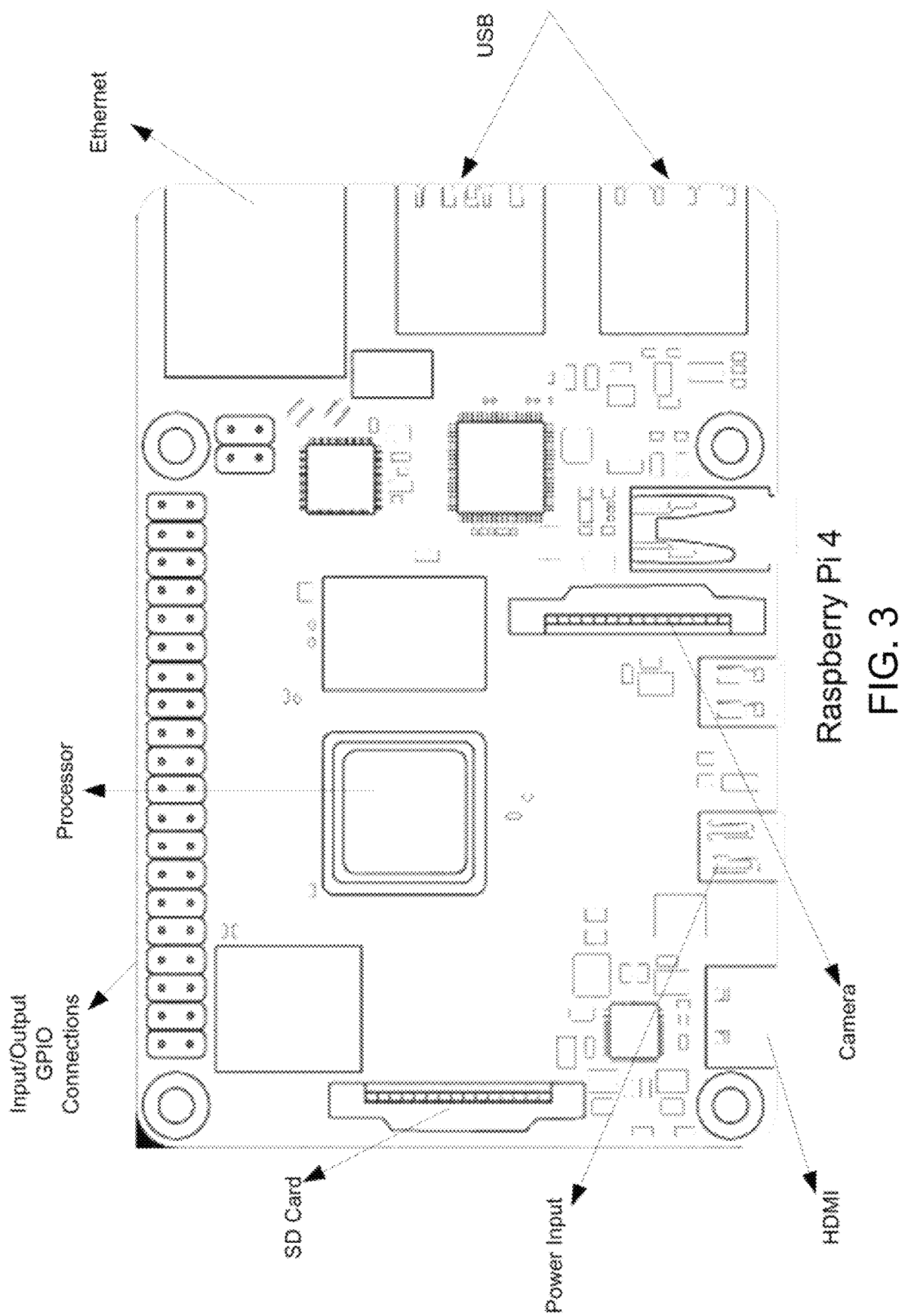
FIG. 3 is diagram of a controller board used in the fabrication of the prototype.
Figure 4:
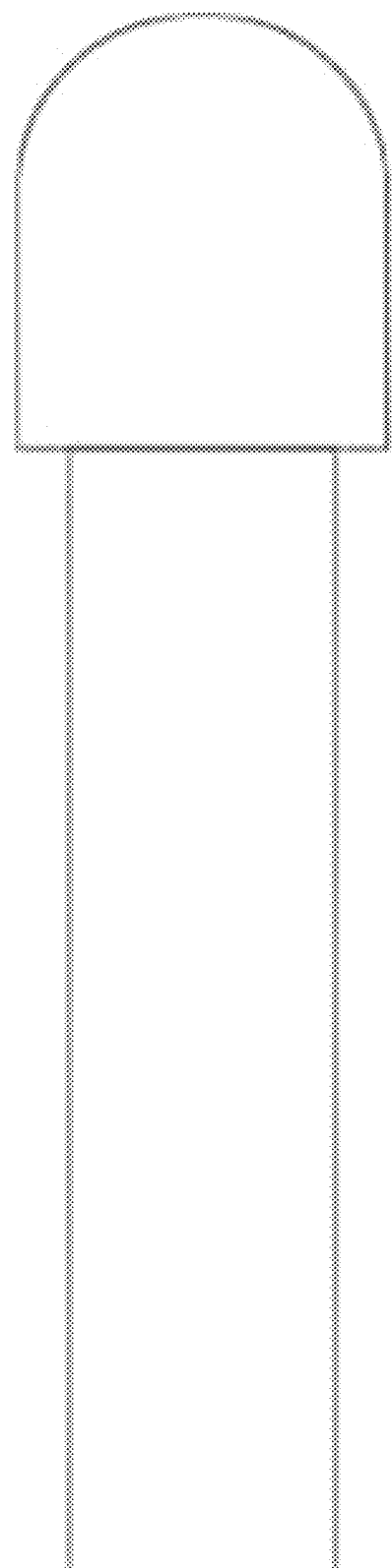
FIG. 4 is diagram of a light emitting diode used in the fabrication of the prototype.
Figure 5:
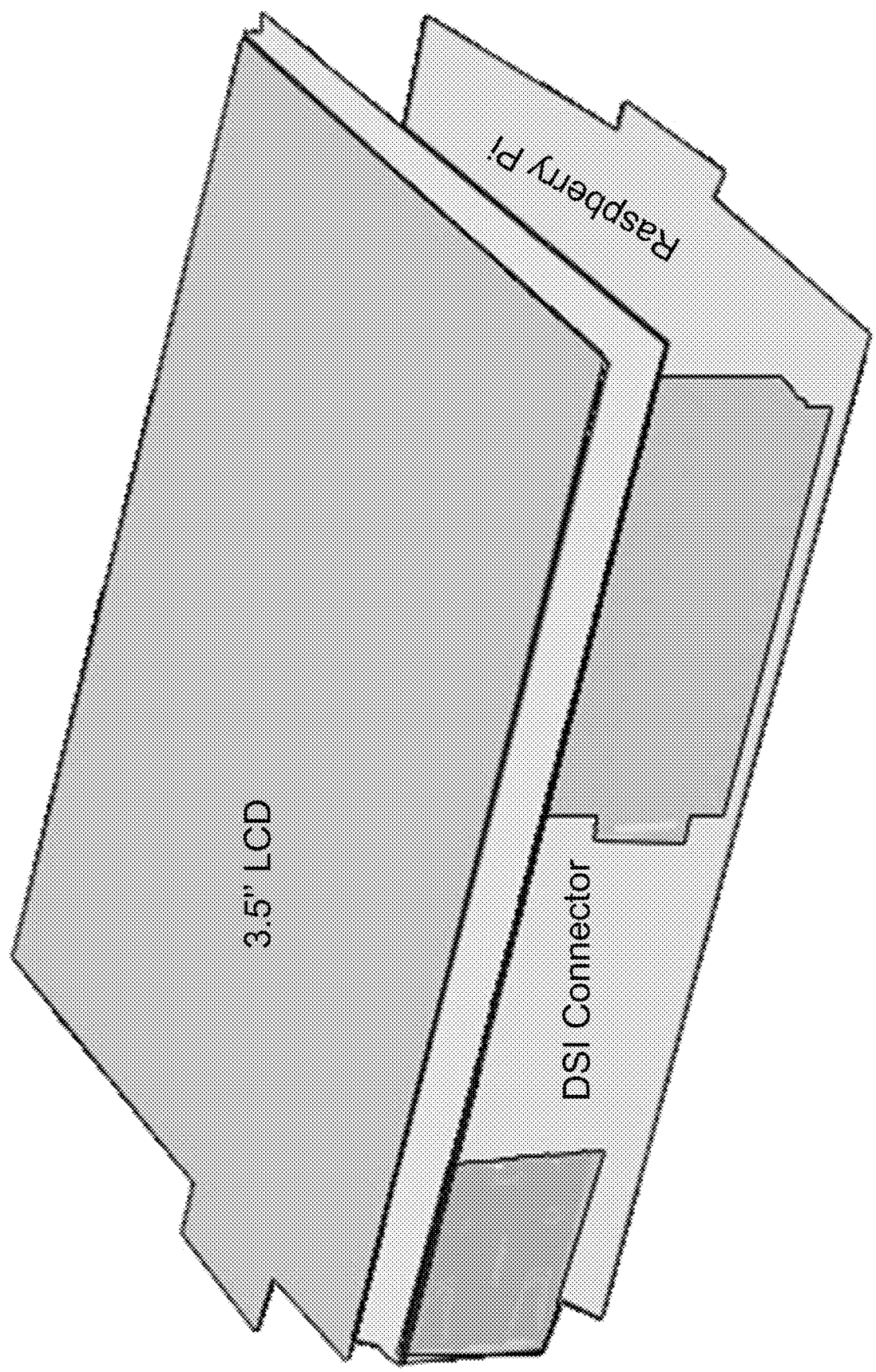
FIG. 5 is diagram of a configuration of the controller board and the display used in the fabrication of the prototype.
Figure 6:
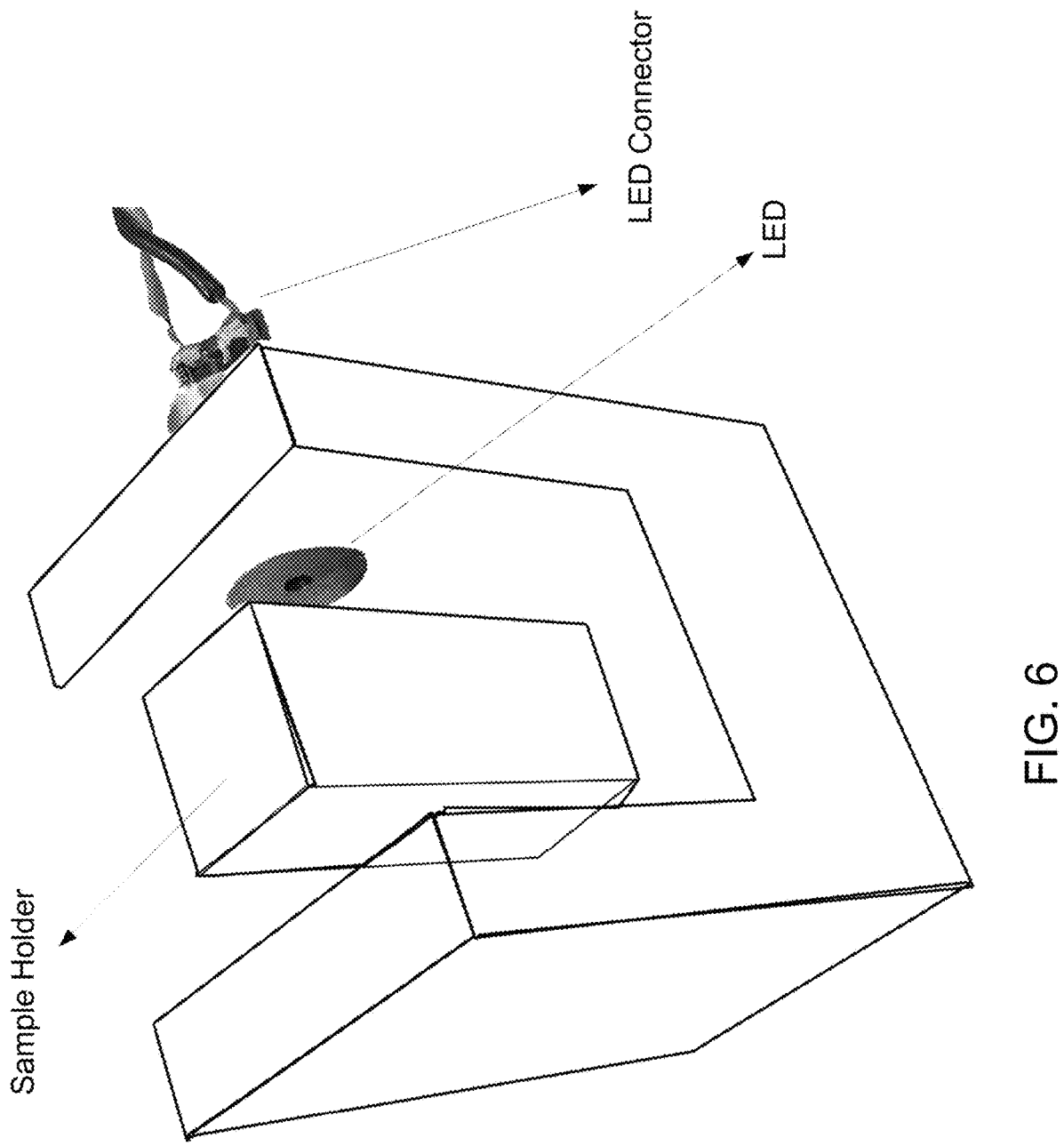
FIG. 6 is diagram of a configuration of the sample holder connected to the light emitting diode used in the fabrication of the prototype.
Figure 7:
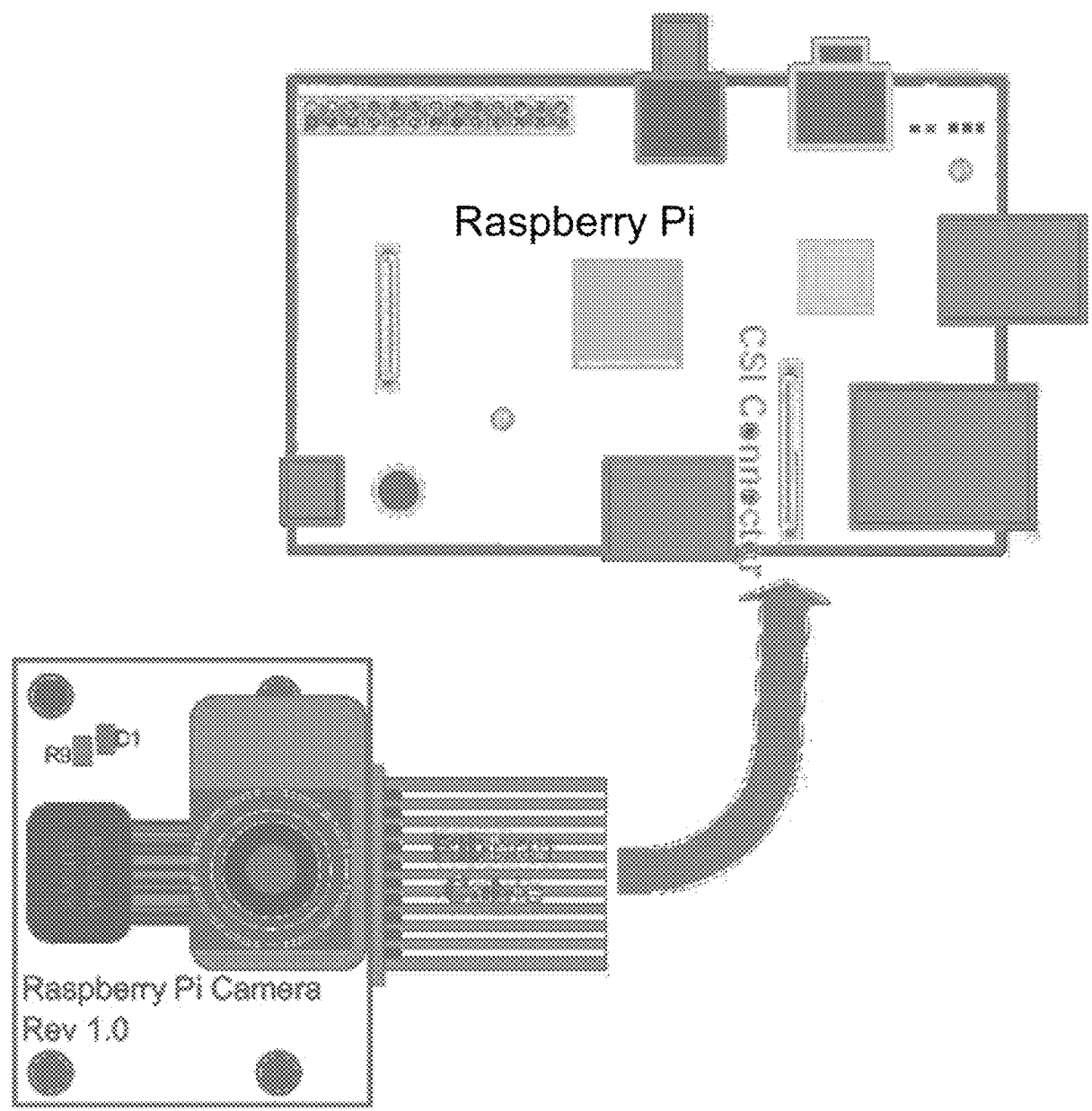
FIG. 7 is diagram of a configuration of the camera connected to the controller board used in the fabrication of the prototype.
Figure 8:
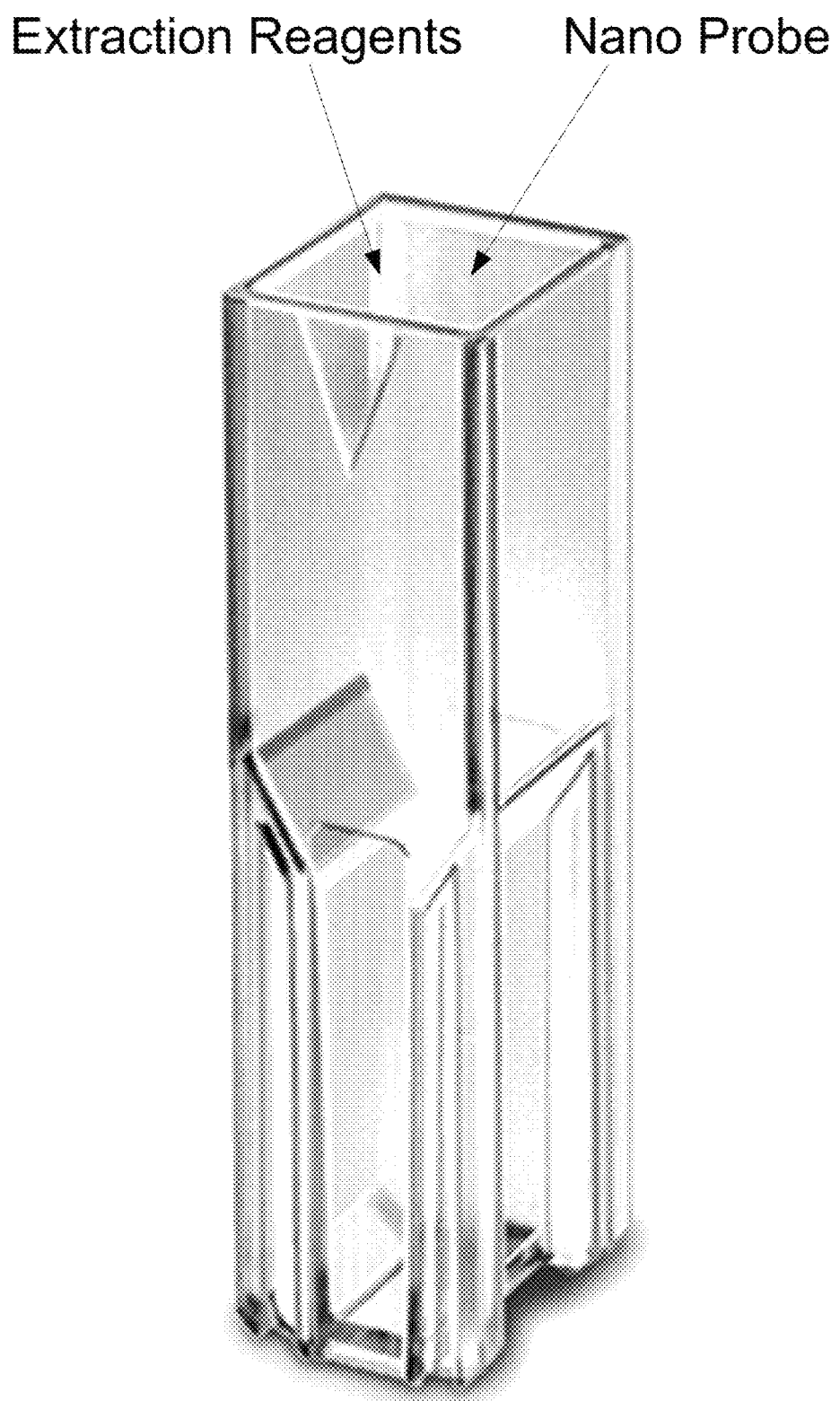
FIG. 8 is diagram of a configuration of the sample holder and nano probe used in the fabrication of the prototype.

The device includes a multipurpose controller board (1.1) for processing and analysis purpose, a camera (1.3) which is integrated with the controller, a resistive touch liquid crystal display (1.7) to view the results (008), a Light emitting diode (1.5) (wavelength in the range of 350 nm-500 nm depending on the toxin of interest) to emit the UV light, Micro secure digital (SD) card (1.6) and a portable power bank (1.2). A plastic cuvette (1.4) can be used as a sample holder.

The device operates (001) using a touch display (1.7) to boot the system (002). The camera (1.3) captures an image in a black box with UV excitation (003) and sends the image (004) to the brain of the device which is controller board (1.1). The image (004) is processed (e.g., in a JPG file). The noise of the image is filtered (005) by using special algorithms (007). Finally, to determine the level of OTA in rice sample, several steps are as follows, i.e. determination of the average pixel value of the image resulted from image segmentation using image processing algorithm (007), conversion of the original image (004), as well as assignment of value. The controller board is programmed in a unique and simple way to extract details (006) of the image (004) using image processing algorithms (007). Based on the programmed algorithm (007), the smart controller (1.1) will analyse the pixel by pixel information of the image (004), which is processed by the controller (1.1), and make a decision on the basis of machine learning algorithms. The process is to determine the center point of identified object to determine the object area. The area is then analyzed to measure the average and deviation standard of pixel values.

EXAMPLE

Experimental Details

A stock standard solution of 1 mg/ml was prepared by dissolving 5 mg of OTA in 5 ml of methanol and then stored at −20° C. OTA solutions in methanol stored at −20° C. are stable over an extended period of time. Working standard solutions in the concentration level of 0.5-200 ng/mL were prepared by diluting the stock solution. pH was adjusted to 7.4. 2 mL of the working standard solutions were added in the plastic cuvettes (1.4) to perform the testing in the prototype (1.8). The prototype (1.8) generated images and RGB were used to build the library.

Use of nano probes in the sensing of analytes has been increased tremendously. Nanomaterial based signal amplification have gained much attention with additional benefits for rapid analysis. Cerium oxide nanoparticles were used to amplify the fluorescence based signal of the tested analyte. A stock standard solution of 1 mg/ml was prepared by dissolving 5 mg OTA in 5 ml of methanol and then stored at −20° C. OTA solutions in methanol stored at −20° C. are stable over an extended period of time. Working standard solution at the concentration level of 5 ng/mL was prepared by diluting the stock solution. pH was adjusted to 7.4. 2 mL of the working standard solutions and nanoceria particle at concentration of 50 ng/mL were added in the plastic cuvettes (1.4) to perform the testing in the prototype (1.8). The prototype (1.8) generated images and RGB were used to build the library.

Acetonitrile was employed as the testing medium. The signal amplification efficiency of two nanoprobes cerium oxide and N-doped titanium oxide nanoparticles was monitored.

a) A stock standard solution of 1 mg/ml was prepared by dissolving 5 mg OTA in 5 ml of methanol and then stored at −20° C. OTA solutions in methanol stored at −20° C. are stable over an extended period of time. Working standard solution at the concentration level of 5 ng/mL was prepared by diluting the stock solution in the solvent acetonitrile-water (6:4, v/v). 2 mL of the working standard solutions in the solvent acetonitrile-water (6:4, v/v), and nanoceria particle at concentration of 50 ng/mL were added in the plastic cuvettes (1.4) to perform the testing in the prototype (1.8). The prototype (1.8) generated images and RGB were used to build the library.

b) A stock standard solution of 1 mg/ml was prepared by dissolving 5 mg OTA in 5 ml of methanol and then stored at −20° C. OTA solutions in methanol stored at −20° C. are stable over an extended period of time. Working standard solution at the concentration level of 5 ng/mL was prepared by diluting the stock solution in the solvent acetonitrile-water (6:4, v/v). 2 mL of the working standard solutions in the solvent acetonitrile-water (6:4, v/v), and N-doped Titanium oxide particle at concentration of 50 ng/mL were added in the plastic cuvettes (1.4) to perform the testing in the prototype (1.8). The prototype (1.8) generated images and RGB were used to build the library.

Food authorities all over the world have established a permissible limit of 3 μg/Kg of OTA in cereal samples. Therefore, OTA at a level of 3 μg/Kg was used to build the library. Certified Rice samples were used to construct the library for future field applications.

a) Sample of rice is finely ground using mortar and pestle and was spiked with OTA at concentration of 3 μg/kg. The weighed crushed rice (2 g) were extracted in 4 mL of solvent mixture of acetonitrile-water (6:4, v/v) in glass vials. Extraction was carried out for 10 min using manual shaking till the clear solvent changes its color to milky solution. Extract was filtered using whattman filter paper (cat. no. 1001 12.5). 2 mL of the filtrate solution were added in the plastic cuvettes (1.4) to perform the testing in the prototype (1.8). The prototype (1.8) generated images and RGB were used to build the library.

b) Sample of rice was finely ground using mortar and pestle and was spiked with OTA at concentration of 3 μg/kg. The weighed crushed rice (2 g) were extracted in 4 mL of solvent mixture of acetonitrile-water (6:4, v/v) in glass vials. Extraction was carried out for 10 min using manual shaking till the clear solvent changes its color to milky solution. Extract was filtered using whattman filter paper (cat. no. 1001 12.5). 2 mL of the filtrate solution and nanoceria particle at concentration of 50 ng/mL were added in the plastic cuvettes (1.4) to perform the testing in the prototype (1.8). The prototype (1.8) generated images and RGB were used to build the library.

c) Sample of rice was finely ground using mortar and pestle and was spiked with OTA at concentration of 3 μg/kg. The weighed crushed rice (2 g) were extracted in 4 mL of solvent mixture of acetonitrile-water (6:4, v/v) in glass vials. Extraction was carried out for 10 min using manual shaking till the clear solvent changes its color to milky solution. Extract was filtered using whattman filter paper (cat. no. 1001 12.5). 2 mL of the filtrate solution and N-doped Titanium oxide at concentration of 50 ng/mL were added in the plastic cuvettes (1.4) to perform the testing in the prototype (1.8). The prototype (1.8) generated images and RGB were used to build the library.

We claim:

1. A fluorescent detector device comprising:
a display interface;
a controller board connected to the display interface, the controller board being configured to perform data processing and pixel analysis that determines average pixel values and deviation standards of pixel values in each different segmentation of images;

a camera integrated with the controller board;

a camera board to support the camera;

a sample holder configured to hold a sample;

a light emitting diode inserted in a wall of the sample holder and located so that the sample held within the sample holder is in front of the light emitting diode, the camera capturing an image of the sample that is excited using light emitted from the light emitted diode, the controller board being configured to perform the data processing and the pixel analysis on the captured image using machine learning algorithms, and the display interface displaying results of the data processing and the pixel analysis on the average pixel values and the deviation standards of pixel values in each different segmentation of the captured image, which indicate a level of Ochratoxin A (OTA) in the sample;

a reagent holder configured to hold extraction reagents and a nano probe; and a power bank configured to supply power to the display interface, the controller board, the camera, the camera board, and the light emitting diode.

2. The device of claim 1, wherein the display interface is a resistive touch liquid crystal display.

3. The device of claim 1, wherein the display interface is attached with the controller board via a Display Serial Interface (DSI).

4. The device of claim 1, wherein the controller board is a single board programmable computer (SBC).

5. The device of claim 1, wherein the camera is attached in a range of 2.5 cm to 3 cm above the sample holder, and a lens or sensor of the camera board is aligned to a center of the sample holder.

6. The device of claim 4, wherein the camera receives the supply of power through a Camera Serial Interface (CSI) from the SBC.

7. The device of claim 1, wherein the light emitting diode has an excitation wavelength between 350-370 nm to excite an analyte and generate a fluorescence image.

8. The device of claim 1, wherein the sample is excited using ultraviolet (UV) light.

9. The device of claim 1, wherein the sample holder holds a cuvette of 2.5 mL.

10. The device of claim 1, wherein the device is used in on-site sample analysis.

11. The device of claim 1, wherein the sample includes Ochratoxin A (OTA).

12. A method of testing Ochratoxin A (OTA), the method comprising:

a) performing extraction on a sample including the OTA with a solvent;

b) inserting the sample into a sample holder using a sample cuvette;

c) adding detection reagent to the sample;

d) exciting the sample using ultraviolet light emitted from a light emitting diode;

e) performing image capturing using a camera on the sample, which is excited by the ultraviolet light, and performing processing and pixel analysis on the captured image using machine learning algorithms by a controller board; and f) displaying results of the data processing and the pixel analysis on average pixel values and deviation standards of pixel values in each different segmentation of the captured image on a display interface of a fluorescent detector device, which indicates a level of the OTA in the sample.

13. The method of claim 12, wherein the solvent is a mixture of acetonitrile-water.

* * * * *